United States Patent
Shimazu et al.

(10) Patent No.: US 7,399,281 B2
(45) Date of Patent: Jul. 15, 2008

(54) PAIN MEASUREMENT SYSTEM AND METHOD OF MEASURING PAIN

(75) Inventors: Hideaki Shimazu, Tokyo (JP); Takeo Ishii, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 571 days.

(21) Appl. No.: 11/012,351

(22) Filed: Dec. 16, 2004

(65) Prior Publication Data

US 2005/0154329 A1  Jul. 14, 2005

(30) Foreign Application Priority Data

Dec. 16, 2003  (JP) ............................. 2003-418652

(51) Int. Cl.
    *A61B 5/00*  (2006.01)
(52) U.S. Cl. ................. 600/557; 600/552; 600/553; 600/554; 600/555
(58) Field of Classification Search ................ 600/557, 600/552, 553, 554, 555

See application file for complete search history.

(56) References Cited

U.S. PATENT DOCUMENTS

| | | | | |
|---|---|---|---|---|
| 4,763,666 A | * | 8/1988 | Strian et al. ................. | 600/554 |
| 5,191,896 A | * | 3/1993 | Gafni et al. ................. | 600/555 |
| 5,363,859 A | * | 11/1994 | Tuckett et al. ............... | 600/552 |
| 5,806,522 A | * | 9/1998 | Katims ........................ | 600/554 |
| 6,113,552 A | * | 9/2000 | Shimazu et al. .............. | 600/557 |
| 6,146,334 A | * | 11/2000 | Laserow ...................... | 600/552 |
| 6,387,054 B1 | | 5/2002 | Laserow | |

* cited by examiner

*Primary Examiner*—Max Hindenburg
*Assistant Examiner*—Sean P Dougherty
(74) *Attorney, Agent, or Firm*—Buchanan Ingersoll & Rooney PC

(57) ABSTRACT

A pain measurement system is capable of accurately and reliably measuring the magnitude of temporary pain in a patient while reducing burdens on the patient during pain measurement. The pain measurement system has a system assembly including a controller that controls an electric stimulus signal output unit to apply a pulse current which increases with time through an electrode. The value of the pulse current is recognized as a minimum sensed current value when a first signal is received. The electric stimulus signal output unit is then controlled to apply, through the electrode, a pulse current having a current value which increases from a predetermined initial value stepwise by nX (where X represents the minimum sensed current value and n represents a positive rational number). The current value of the pulse current is recognized as a pain-commensurate current value when a second signal is received.

17 Claims, 9 Drawing Sheets

F I G. 1
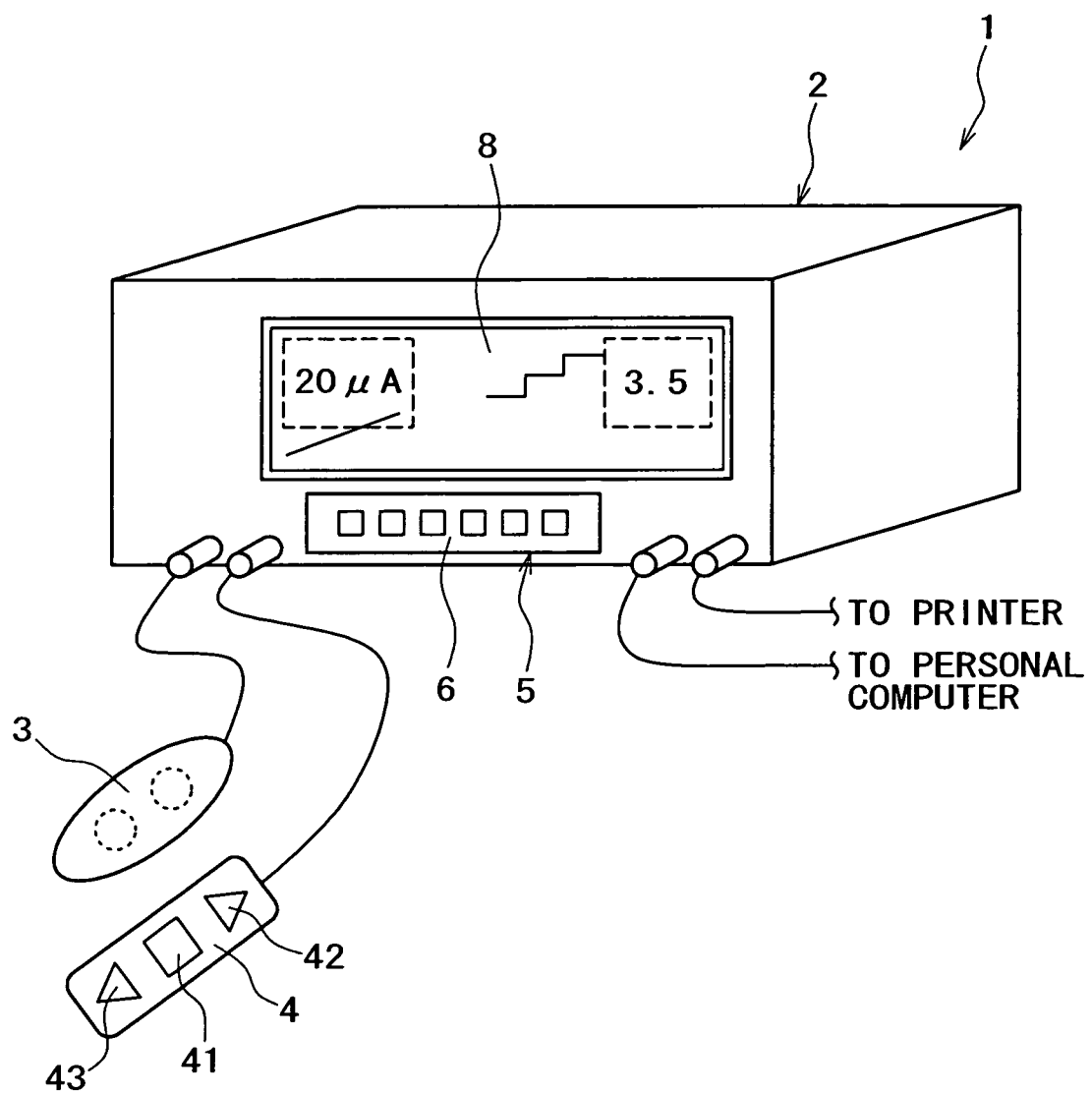

FIG. 9
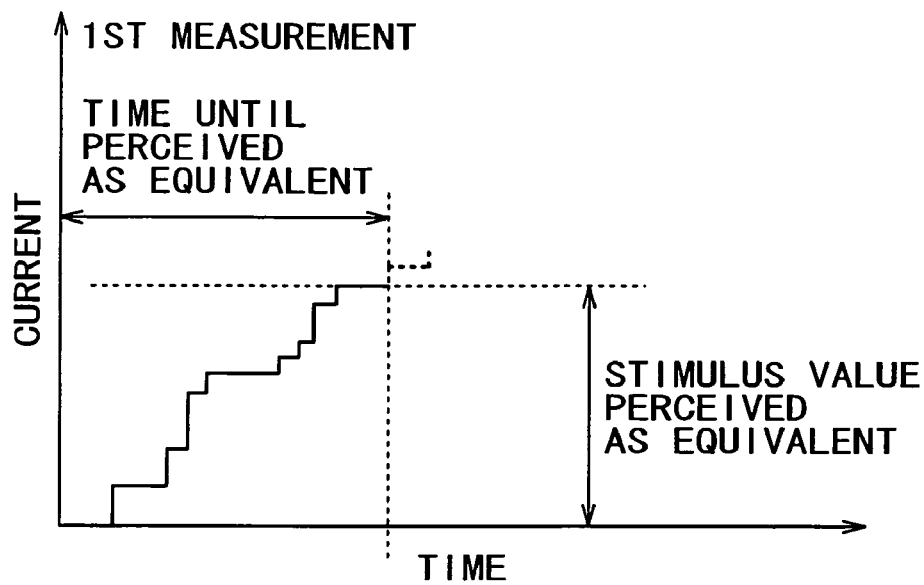
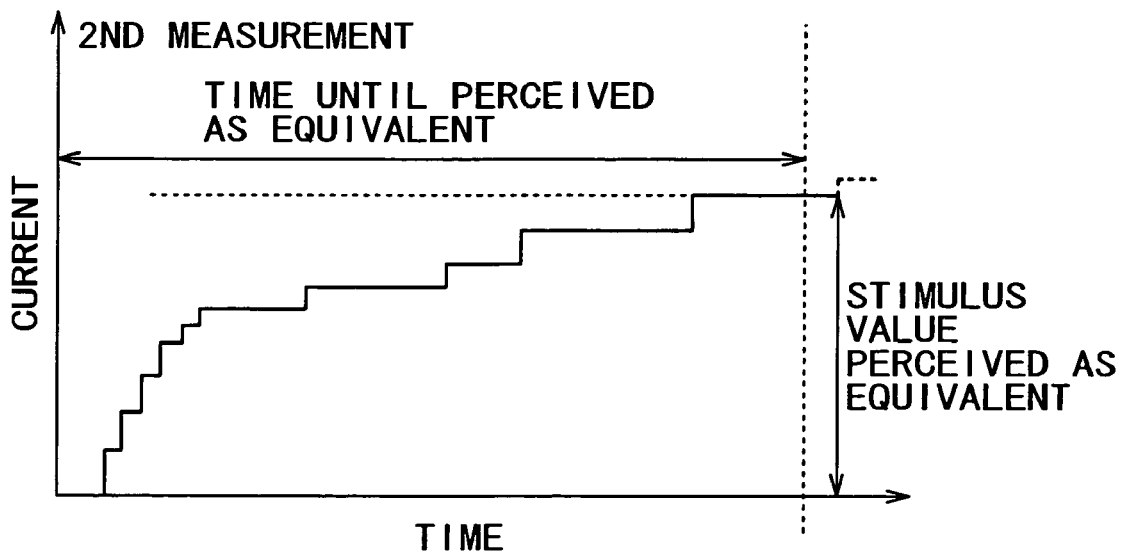

2

PAIN MEASUREMENT SYSTEM AND METHOD OF MEASURING PAIN

BACKGROUND OF THE INVENTION

1. Field of the Invention

The present invention relates to a pain measurement system and a method of measuring pain.

2. Description of the Related Art

Pain can be described generally in two ways. According to one approach, pain is expressed in terms of quality or type. For example, pain may be described as "burning pain", "smarting pain", "pricking pain", etc. The other way of describing pain is based on the magnitude of pain. For example, pain may be described as "slight pain", "unbearable pain", etc.

The former pain expressions can easily be made if one is aware of a certain range of modifying words for pain. However, it is difficult to properly express magnitudes of pain because the sensation of pain is subjective and personal, and the degree to which one can tolerate pain is easily affected by cultural and psychological factors.

Nevertheless, an objective evaluation of pain is indispensable for diagnosing pain and judging therapeutic effects.

Heretofore, a visual analog scale based on an evaluation made by a patient has been used to determine the magnitude of a pain felt by the patient. For example, a straight line that is 10 cm long is drawn on a sheet of paper with one end of the line representing no pain and the other end intolerable pain. The patient puts a mark indicative of the magnitude of a pain actually felt by the patient on the straight line at a commensurate position along the scale of the straight line.

Although the above evaluating method is simple, it is subjective and has evaluation standards varying from patient to patient. This makes it difficult to compare measured magnitudes of pain between different patients.

Attempts have been made to measure a pain in terms of physiological reactions such as aspiration, heartbeat, blood pressure, etc. for objectively expressing the pain. However, those efforts have proven unsuccessful.

SUMMARY OF THE INVENTION

According to the present invention, a pain measurement system is provided for measuring a magnitude of pain experienced by an examinee, comprising stimulus applying means for applying a stimulus, a stimulus output unit for outputting a stimulus to the stimulus applying means, a control unit for controlling an output of the stimulus output unit, and a console for sending a signal to the control unit to time the control unit to recognize the value of the stimulus applied by the stimulus applying means, the control unit comprising first means for controlling the stimulus output unit to cause the stimulus applying means to apply a stimulus having a magnitude which increases with time, second means for recognizing the value of the stimulus applied by the stimulus applying means as a first stimulus value when a first signal is received from the console, third means for controlling the stimulus output unit to cause the stimulus applying means to apply a stimulus having a magnitude which increases from a predetermined initial value stepwise by nX (where X represents the first stimulus value and n represents a positive rational number), and fourth means for recognizing the value of the stimulus applied by the stimulus applying means as a second stimulus value when a second signal is received from the console.

The console may have a stop switch for causing the stimulus applying means to stop applying the stimulus.

According to the present invention, there is also provided a pain measurement system for measuring a magnitude of pain experienced by an examinee, comprising stimulus applying means for applying a stimulus, a stimulus output unit for outputting a stimulus to the stimulus applying means, a control unit for controlling an output of the stimulus output unit, and a console for sending a signal to the control unit to time the control unit to recognize the value of the stimulus applied by the stimulus applying means, the control unit comprising first means for controlling the stimulus output unit to cause the stimulus applying means to apply a stimulus having a magnitude which increases with time, second means for recognizing the value of the stimulus applied by the stimulus applying means as a first stimulus value when a first signal is received from the console, third means for selectively performing a step-up control mode for controlling the stimulus output unit to cause the stimulus applying means to apply a stimulus having a magnitude which increases from a predetermined initial value stepwise by nX (where X represents the first stimulus value and n represents a positive rational number), and a step-down control mode for controlling the stimulus output unit to cause the stimulus applying means to apply a stimulus having a magnitude which decreases stepwise by nX, and fourth means for recognizing the value of the stimulus applied by the stimulus applying means as a second stimulus value when a second signal is received from the console.

The third means may first perform the step-up control mode.

When one of the step-up control mode and the step-down control mode switches to the other, the third means may change the value of n to a value smaller than that which was used prior to the switching.

The console may have a stop switch for causing the stimulus applying means to stop applying the stimulus, and a mode selector switch for switching between the step-up control mode and the step-down control mode.

When the first means is in operation, if the stop switch is operated, the console may send the first signal to the control unit.

When the third means is in operation, if the stop switch is operated, the console may send the second signal to the control unit.

When the third means is in operation, the stimulus applied by the stimulus applying means may have an initial value of 2nX.

The value of n may be integral number.

The value of n may be in the range from 0.1 to 2.0.

The value of n may be adjustable.

The stimulus applied by the stimulus applying means may have a maximum value of 10×.

The stimulus applied by the stimulus applying means may have a frequency in the range from 30 to 100 times/second, and the stimulating time per stimulus can be in the range from 0.1 to 5 millisecond/stimulus.

When the third means is in operation, the time during which the magnitude of the stimulus applied by the stimulus applying means stays in each step may be adjustable in the range from 1 to 30 seconds.

When the first means is in operation, the magnitude of the stimulus applied by the stimulus applying means may increase continuously at a substantially constant rate.

The stimulus may comprise an electric stimulus, and the stimulus applying means may comprise an electrode.

The stimulus may comprise a painless stimulus.

According to the present invention, there is further provided a pain measurement system for measuring a magnitude of pain experienced by an examinee, comprising a vibrating device for applying a vibratory stimulus, an electric power supply for supplying electric power to the vibrating device, a control unit for controlling the electric power supply, and a console for sending a signal to the control unit to time the control unit to recognize the value of the vibratory stimulus applied by the vibrating device, the control unit comprising first means for controlling the electric power supply to cause the vibrating device to apply a vibratory stimulus having a magnitude which increases with time, second means for recognizing the value of the vibratory stimulus applied by the vibrating device as a first stimulus value when a first signal is received from the console, third means for selectively performing a step-up control mode for controlling the electric power supply to cause the vibrating device to apply a vibratory stimulus having a magnitude which increases from a predetermined initial value stepwise by nX (where X represents the first stimulus value and n represents a positive rational number), and a step-down control mode for controlling the electric power supply to cause the vibrating device to apply a vibratory stimulus having a magnitude which decreases stepwise by nX, and fourth means for recognizing the value of the vibratory stimulus applied by the vibrating device as a second stimulus value when a second signal is received from the console.

The pain measurement system may have recording means for recording the first stimulus value and/or a value corresponding to the first stimulus value, and display means for displaying the first stimulus value and/or the value corresponding to the first stimulus value and also displaying a value, which is produced by dividing the second stimulus value by the first stimulus value, or a value corresponding to the value produced by dividing the second stimulus value by the first stimulus value, as a pain ratio.

According to the present invention, there is further provided a pain measurement system for measuring a magnitude of pain experienced by an examinee, comprising stimulus applying means for applying a stimulus, a stimulus output unit for outputting a stimulus to the stimulus applying means, a control unit for controlling an output of the stimulus output unit, and a console, the control unit comprising means for controlling the stimulus output unit to cause the stimulus applying means to apply a stimulus having a substantially constant magnitude, means for controlling the stimulus output unit to cause the stimulus applying means to stop applying a stimulus, and means for controlling the stimulus output unit to cause the stimulus applying means to start applying a stimulus having a magnitude which is a predetermined amount greater than before the stimulus applying means stops applying the stimulus.

According to the present invention, there is also provided a pain measurement system for measuring a magnitude of pain experienced by an examinee, comprising stimulus applying means for applying a stimulus, a stimulus output unit for outputting a stimulus to the stimulus applying means, a control unit for controlling an output of the stimulus output unit, and a console, the control unit comprising means for selectively performing a step-up control mode for controlling the stimulus output unit to cause the stimulus applying means to apply a stimulus having a magnitude which increases stepwise, and a step-down control mode for controlling the stimulus output unit to cause the stimulus applying means to apply a stimulus having a magnitude which decreases stepwise.

According to the present invention, there is also provided a pain measurement system for measuring a magnitude of pain experienced by an examinee, comprising stimulus applying means for applying a stimulus, a stimulus output unit for outputting a stimulus to the stimulus applying means, a control unit for controlling an output of the stimulus output unit, and a console for sending a signal to the control unit to time the control unit to recognize the value of the stimulus applied by the stimulus applying means, the control unit comprising first means for controlling the stimulus output unit to cause the stimulus applying means to apply a stimulus having a magnitude which increases with time, second means for recognizing the value of the stimulus applied by the stimulus applying means as a first stimulus value when a first signal is received from the console, third means for controlling the stimulus output unit to cause the stimulus applying means to apply a stimulus having a magnitude which increases from a predetermined initial value stepwise by nX (where X represents the first stimulus value and n represents a positive rational number) and which persists for a variable amount of time in each step, and fourth means for recognizing the value of the stimulus applied by the stimulus applying means as a second stimulus value when a second signal is received from the console.

When the third means is in operation, the time during which the magnitude of the stimulus applied by the stimulus applying means persists in each step may increase gradually.

According to the present invention, there is further provided a pain measurement system for measuring a magnitude of pain experienced by an examinee in at least two measuring processes, comprising stimulus applying means for applying a stimulus, a stimulus output unit for outputting a stimulus to the stimulus applying means, a control unit for controlling an output of the stimulus output unit, and a console for sending a signal to the control unit to time the control unit to recognize the value of the stimulus applied by the stimulus applying means, the control unit comprising means for controlling the stimulus output unit in a first measuring process to cause the stimulus applying means to apply a stimulus having a magnitude which increases with time, means for recognizing the value of the stimulus applied by the stimulus applying means as a first stimulus value when a first signal is received from the console, means for controlling the stimulus output unit in a second measuring process to cause the stimulus applying means to apply a stimulus having a magnitude which increases with time at a rate smaller than the rate at which the magnitude of the stimulus increases in the first measuring process, before the magnitude of the stimulus reaches the first stimulus value, and means for recognizing the value of the stimulus applied by the stimulus applying means as a second stimulus value when a second signal is received from the console.

In the first measuring process, the magnitude of the stimulus applied by the stimulus applying means may increase continuously or stepwise.

In the second measuring process, the magnitude of the stimulus applied by the stimulus applying means may increase continuously or stepwise.

According to the present invention, there is further provided a pain measurement system for measuring a magnitude of pain experienced by an examinee in at least two measuring processes, comprising stimulus applying means for applying a stimulus, a stimulus output unit for outputting a stimulus to the stimulus applying means, a control unit for controlling an output of the stimulus output unit, and a console for sending a signal to the control unit to time the control unit to recognize the value of the stimulus applied by the stimulus applying means, the control unit comprising means for controlling the stimulus output unit in a first measuring process to cause the stimulus applying means to apply a stimulus having a magnitude which increases irregularity with time, means for recognizing the value of the stimulus applied by the stimulus applying means as a first signal is received from the console, means for controlling the stimulus output unit in a second measuring process to cause the stimulus applying means to apply a stimulus having a magnitude which increases with time and which reaches the first stimulus value in a time different from the time required for the magnitude of the stimulus applied by the stimulus applying means to reach the first stimulus value in the first measuring process, and means for recognizing the value of the stimulus applied by the stimulus applying means as a second stimulus value when a second signal is received from the console.

In the first measuring process, the magnitude of the stimulus applied by the stimulus applying means may increase stepwise, and an increase per step in the magnitude of the stimulus and the time during which the magnitude of the stimulus may persist in each step increase and decrease irregularity.

In the second measuring process, the magnitude of the stimulus applied by the stimulus applying means may increase stepwise, and an increase per step in the magnitude of the stimulus and the time during which the magnitude of the stimulus may persist in each step increase and decrease irregularity.

The stimulus may comprise an electric stimulus, and the stimulus applying means may comprise an electrode.

The stimulus preferably comprises a painless stimulus.

According to the present invention, there is also provided a method of measuring a magnitude of pain experienced by an examinee with a pain measurement system having stimulus applying means for applying a stimulus, a stimulus output unit for outputting a stimulus to the stimulus applying means, a control unit for controlling an output of the stimulus output unit, and a console for sending a signal to the control unit to time the control unit to recognize the value of the stimulus applied by the stimulus applying means, the method comprising the steps of controlling the stimulus output unit to cause the stimulus applying means to apply a stimulus having a magnitude which increases with time, recognizing the value of the stimulus applied by the stimulus applying means as a first stimulus value when a first signal is received from the console, controlling the stimulus output unit to cause the stimulus applying means to apply a stimulus having a magnitude which increases from a predetermined initial value stepwise by nX (where X represents the first stimulus value and n represents a positive rational number), and recognizing the value of the stimulus applied by the stimulus applying means as a second stimulus value when a second signal is received from the console.

According to the present invention, there is also provided a method of measuring a magnitude of pain experienced by an examinee with a pain measurement system having stimulus applying means for applying a stimulus, a stimulus output unit for outputting a stimulus to the stimulus applying means, a control unit for controlling an output of the stimulus output unit, and a console for sending a signal to the control unit to time the control unit to recognize the value of the stimulus applied by the stimulus applying means, the method comprising the steps of controlling the stimulus output unit to cause the stimulus applying means to apply a stimulus having a magnitude which increases with time, recognizing the value of the stimulus applied by the stimulus applying means as a first stimulus value when a first signal is received from the console, selectively performing a step-up control mode for controlling the stimulus output unit to cause the stimulus applying means to apply a stimulus having a magnitude which increases from a predetermined initial value stepwise by nX (where X represents the first stimulus value and n represents a positive rational number), and a step-down control mode for controlling the stimulus output unit to cause the stimulus applying means to apply a stimulus having a magnitude which decreases stepwise by nX, and recognizing the value of the stimulus applied by the stimulus applying means as a second stimulus value when a second signal is received from the console.

When one of the step-up control mode and the step-down control mode switches to the other, the value of n changes to a value smaller than that which was used prior to the switching.

According to the present invention, there is also provided a method of measuring a magnitude of pain experienced by an examinee with a pain measurement system having a vibrating device for applying a vibratory stimulus, an electric power supply for supplying electric power to the vibrating device, a control unit for controlling the electric power supply, and a console for sending a signal to the control unit to time the control unit to recognize the value of the vibratory stimulus applied by the vibrating device, the method comprising the steps of controlling the electric power supply to cause the vibrating device to apply a vibratory stimulus having a magnitude which increases with time, recognizing the value of the vibratory stimulus applied by the vibrating device as a first stimulus value when a first signal is received from the console, selectively performing a step-up control mode for controlling the electric power supply to cause the vibrating device to apply a vibratory stimulus having a magnitude which increases from a predetermined initial value stepwise by nX (where X represents the first stimulus value and n represents a positive rational number), and a step-down control mode for controlling the electric power supply to cause the vibrating device to apply a vibratory stimulus having a magnitude which decreases stepwise by nX, and recognizing the value of the vibratory stimulus applied by the vibrating device as a second stimulus value when a second signal is received from the console.

According to the present invention, there is further provided a method of measuring a magnitude of pain experienced by an examinee with a pain measurement system having stimulus applying means for applying a stimulus, a stimulus output unit for outputting a stimulus to the stimulus applying means, a control unit for controlling an output of the stimulus output unit, and a console, the method comprising the steps of controlling the stimulus output unit to cause the stimulus applying means to apply a stimulus having a substantially constant magnitude, controlling the stimulus output unit to cause the stimulus applying means to stop applying a stimulus, and controlling the stimulus output unit to cause the stimulus applying means to start applying a stimulus having a magnitude which is a predetermined amount greater than before the stimulus applying means stops applying the stimulus.

According to the present invention, there is further provided a method of measuring a magnitude of pain experienced by an examinee with a pain measurement system having stimulus applying means for applying a stimulus, a stimulus output unit for outputting a stimulus to the stimulus applying means, a control unit for controlling an output of the stimulus output unit, and a console, the method comprising the steps of selectively performing a step-up control mode for controlling the stimulus output unit to cause the stimulus applying means to apply a stimulus having a magnitude which increases stepwise, and a step-down control mode for controlling the stimulus output unit to cause the stimulus applying means to apply a stimulus having a magnitude which decreases stepwise.

According to the present invention, there is further provided a method of measuring a magnitude of pain experienced by an examinee with a pain measurement system having stimulus applying means for applying a stimulus, a stimulus output unit for outputting a stimulus to the stimulus applying means, a control unit for controlling an output of the stimulus output unit, and a console for sending a signal to the control unit to time the control unit to recognize the value of the stimulus applied by the stimulus applying means, the method comprising the steps of controlling the stimulus output unit to cause the stimulus applying means to apply a stimulus having a magnitude which increases with time, recognizing the value of the stimulus applied by the stimulus applying means as a first stimulus value when a first signal is received from the console, controlling the stimulus output unit to cause the stimulus applying means to apply a stimulus having a magnitude which increases from a predetermined initial value stepwise by nX (where X represents the first stimulus value and n represents a positive rational number) and which persists for a variable amount of time in each step, and recognizing the value of the stimulus applied by the stimulus applying means as a second stimulus value when a second signal is received from the console.

According to the present invention, there is also provided a method of measuring a magnitude of pain experienced by an examinee in at least two measuring processes with a pain measurement system having stimulus applying means for applying a stimulus, a stimulus output unit for outputting a stimulus to the stimulus applying means, a control unit for controlling an output of the stimulus output unit, and a console for sending a signal to the control unit to time the control unit to recognize the value of the stimulus applied by the stimulus applying means, the method comprising the steps of controlling the stimulus output unit in a first measuring process to cause the stimulus applying means to apply a stimulus having a magnitude which increases with time, recognizing the value of the stimulus applied by the stimulus applying means as a first stimulus value when a first signal is received from the console, controlling the stimulus output unit in a second measuring process to cause the stimulus applying means to apply a stimulus having a magnitude which increases with time at a rate smaller than the rate at which the magnitude of the stimulus increases in the first measuring process, before the magnitude of the stimulus reaches the first stimulus value, and recognizing the value of the stimulus applied by the stimulus applying means as a second stimulus value when a second signal is received from the console.

According to the present invention, there is also provided a method of measuring a magnitude of pain experienced by an examinee in at least two measuring processes with a pain measurement system having stimulus applying means for applying a stimulus, a stimulus output unit for outputting a stimulus to the stimulus applying means, a control unit for controlling an output of the stimulus output unit, and a console for sending a signal to the control unit to time the control unit to recognize the value of the stimulus applied by the stimulus applying means, the method comprising the steps of controlling the stimulus output unit in a first measuring process to cause the stimulus applying means to apply a stimulus having a magnitude which increases irregularly with time, recognizing the value of the stimulus applied by the stimulus applying means as a first stimulus value when a first signal is received from the console, controlling the stimulus output unit in a second measuring process to cause the stimulus applying means to apply a stimulus having a magnitude which increases with time and which reaches the first stimulus value in a time different from the time required for the magnitude of the stimulus applied by the stimulus applying means to reach the first stimulus value in the first measuring process, and recognizing the value of the stimulus applied by the stimulus applying means as a second stimulus value when a second signal is received from the console.

According to the present invention, there is also provided a method of measuring a magnitude of pain experienced by an examinee, the method comprising the steps of applying a stimulus having a magnitude which increases with time, recognizing the value of the stimulus as a first stimulus value when the examinee receives a stimulus for the first time, applying a stimulus having a magnitude which increases from a predetermined initial value stepwise by nX where X represents said first stimulus value and n represents a positive rational number, comparing a magnitude of the stimulus to the magnitude of pain experienced by the examinee, and recognizing the value of the stimulus as a second stimulus value when the examinee judges that the compared magnitudes are the same as each other.

The above and other objects, features, and advantages of the present invention will become apparent from the following description when taken in conjunction with the accompanying drawings which illustrate preferred embodiments of the present invention by way of example.

BRIEF DESCRIPTION OF THE DRAWINGS

FIG. 1 is a perspective view of a pain measurement system according to a first embodiment of the present invention;

FIG. 9 is a diagram illustrative of the manner in which a pain measurement system according to a fourth embodiment of the present invention operates.

DETAILED DESCRIPTION OF PREFERRED EMBODIMENTS

Figure 2:
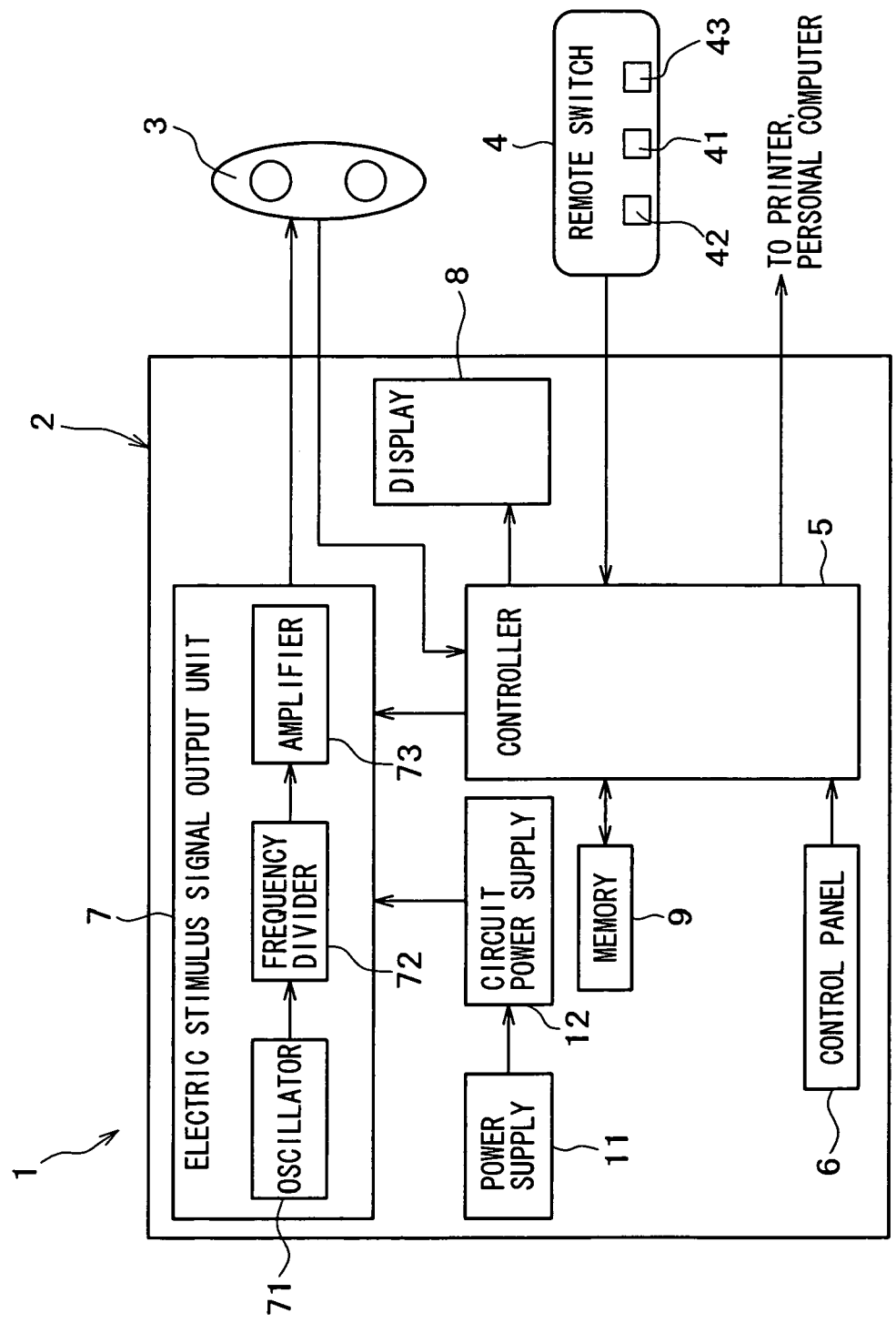
FIG. 2 is a block diagram of a circuit arrangement of the pain measurement system shown in FIG. 1.
Figure 3:
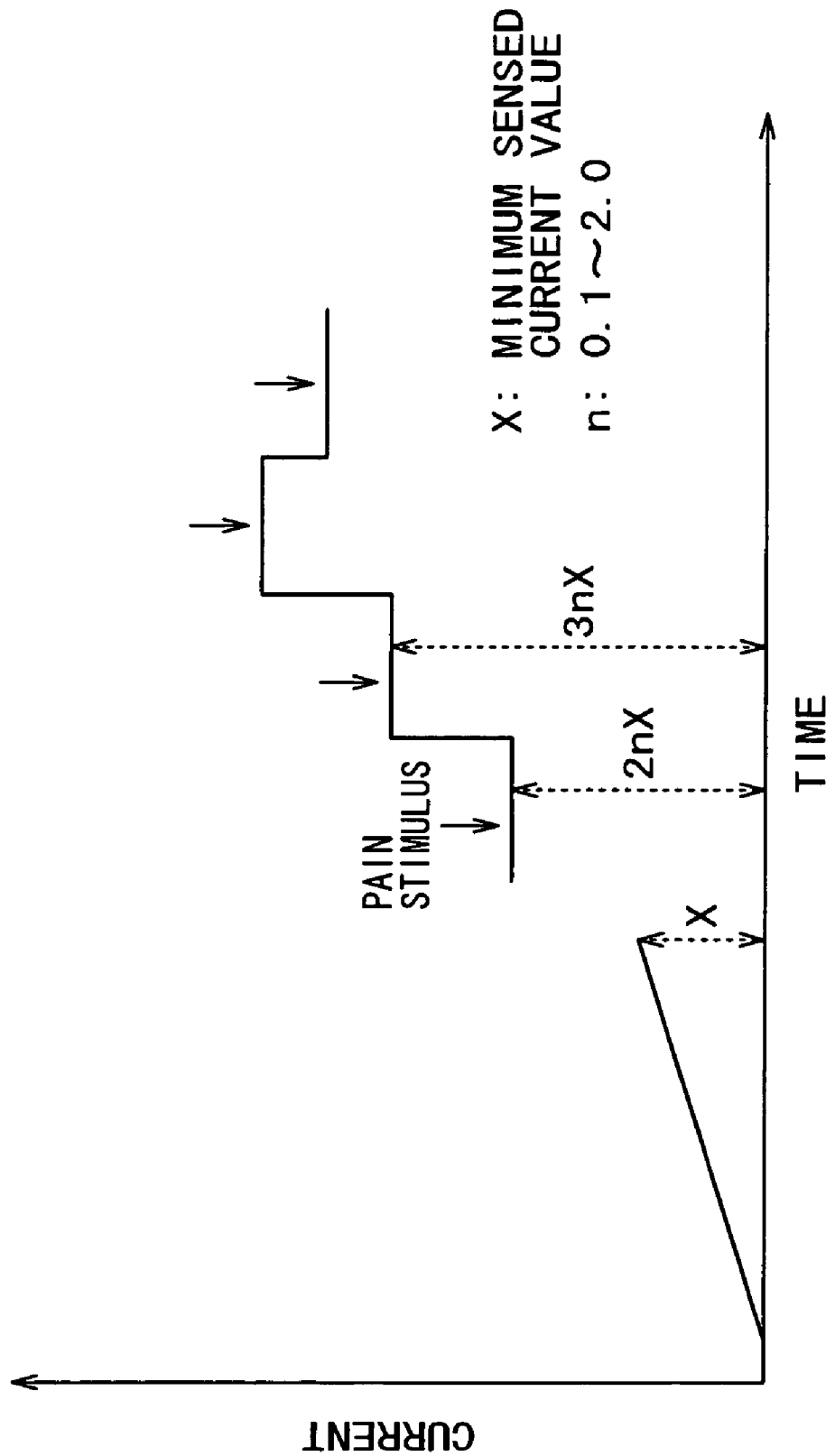
FIG. 3 is a diagram illustrative of the manner in which the pain measurement system shown in FIG. 1 operates.

A pain measurement system 1 according to a first embodiment of the present invention as shown in FIGS. 1 through 3 applies an electric stimulus (an electric stimulative sensation), particularly a painless electric stimulus (painless stimulus), which is different from pain experienced by a patient (examinee). The system 1 compares the magnitude of the electric stimulus and the magnitude of actual pain (measured pain) to quantify the magnitude of the pain in the patient.

When a certain electric stimulus (a current under certain conditions) is applied to a patient, the patient develops a painless sensation such as a numb sensation (vibratory sensation). When the electric stimulus, i.e., the magnitude of the current, increases or decreases, the magnitude of the sensation developed by the patient also increases or decreases. Therefore, the magnitude of pain can be measured without having the patient feel pain due to the measurement, by comparing the magnitude of the electric stimulus (the sensation developed by the patient) to the magnitude of pain.

As shown in FIGS. 1 and 2, the pain measurement system 1 has a system assembly 2 having a casing, an electrode (stimulus applying means) 3 removably attached to a patient (examinee), and a remote switch (console) 4 operated by the patient. The electrode 3 is electrically connected to the system assembly 2 by a lead wire. The remote switch 4 is electrically connected to the system assembly 2 by a lead wire. These components of the pain measurement system 1 will be described below.

The system assembly 2 has a controller 5, a control panel (console) 6, an electric stimulus signal output unit 7 for outputting an electric stimulus in the form of a pulse current to the electrode 3, a display unit 8, a memory 9, a power supply 11, and a circuit power supply 12. External devices including a printer, a personal computer, etc., for example, can removably be electrically connected to the system assembly 2.

The controller 5 has a microcomputer and controls overall operation of the pain measurement system 1 including the electric stimulus signal output unit 7, the display unit 8, the memory 9, etc.

The memory 9 comprises a semiconductor memory such as a ROM, a flash memory, an EEPROM, a RAM or the like. The memory 9 stores various programs including a program for controlling operation of the pain measurement system 1. The memory 9 also stores various data of measured results representing a minimum sensed current value (minimum sensed stimulus value, or first stimulus value), a current value having a magnitude equivalent to the magnitude of a pain, i.e., a pain-commensurate current value (second stimulus value), a pain ratio, and values corresponding to these values. The program and the data are read from the memory 9 when necessary.

The pain ratio is a value produced by dividing the pain-commensurate current value (second stimulus value) by the minimum sensed current value (first stimulus value). Alternatively, a value corresponding to the value produced by dividing the pain-commensurate current value by the minimum sensed current value may be used as the pain ratio.

The display unit 8 comprises a liquid crystal display panel, an EL display panel, or the like, for example. The display unit 8 displays necessary information from various items of information (data), such as the measured results representing the minimum sensed current value (minimum sensed stimulus value, or first stimulus value), the pain-commensurate current value (second stimulus value), the pain ratio, etc., time-dependent changes in the current values (current intensities), measuring conditions, warnings, etc.

The necessary information can be read by a personal computer connected to the system assembly 2, and can be totaled and recorded by the personal computer. The necessary information can also be printed by a printer connected to the system assembly 2.

The electric stimulus signal output unit 7 comprises an oscillator 71, a frequency divider 72, and an amplifier 73.

The oscillator 71 of the electric stimulus signal output unit 7 is oscillated at a certain frequency, e.g., a frequency of 50 Hz, to generate a signal. The frequency divider 72 generates a rectangular wave having a certain pulse duration, e.g., a pulse duration of 2 milliseconds, from the signal generated by the oscillator 71. The generated rectangular wave is amplified by the amplifier 73 and output therefrom as a pulse current or voltage. The pulse current from the amplifier 73 is finally applied as an electric stimulus (stimulus signal) through the electrode 3 to a certain region of the patient.

Although the pulse signal output from the electric stimulus signal output unit 7 is in the form of a rectangular wave, its waveform is deformed when it is applied to the patient because the pulse signal is affected by the patient. Specifically, the pulse current measured from the patient has a sawtooth waveform where one corner of each peak of the rectangular wave is removed.

If the pulse signal output from the electric stimulus signal output unit 7 has a frequency of 50 Hz and a pulse duration of 2 milliseconds, then the measured current having a sawtooth waveform has a pulse duration of 0.5 millisecond in the vicinity of the effective value thereof. The frequency of the pulse signal output from the electric stimulus signal output unit 7 is selected to be 50 Hz because that frequency is frequently used in medical low-frequency therapeutic devices, and is effective to eliminate electric stimulus pain when combined with the sawtooth current waveform. Such a specific condition for eliminating electric stimulus pain is illustrated by way of example only.

The electrode 3 may be of any of various forms, such as a bipolar adhesive electrode or the like. If the electrode 3 comprises a bipolar adhesive electrode, then an electrically conductive gel is preferably used as the adhesive.

As described above, the electrode 3 applies an electric stimulus in the form of a pulse current, particularly, a painless electric stimulus (painless stimulus), to the patient. The magnitude of the current flowing in the patient is detected through the electrode 3 by the controller 5.

The pulse current applied by the electrode 3 preferably has a frequency (stimulus frequency) in the range from 30 to 100 Hz (30 to 100 times/second), and a pulse duration (stimulating time per stimulus) in the range from 0.1 to 5 milliseconds (0.1 to 5 milliseconds/stimulus).

In this manner, a substantially painless electric stimulus can be applied to the patient, although it also depends on other conditions.

The control panel 6 has various setting switches and dials for making various settings including a current increasing rate (rate for increasing the magnitude of a stimulus), a multiple (n value) of a minimum sensed current value, etc., and control switches including a start switch, a pause switch, a stop switch, a reset switch, etc. Signals output from the control panel 6 are input to the controller 5, which perform predetermined processing sequences depending on those signals.

The remote switch 4 has control switches including a stop switch 41, a step-up switch 42, and a step-down switch 43. Signals output from the remote switch 4 are transmitted to the controller 5, which perform predetermined processing sequences depending on those signals.

When the stop switch 41 of the remote switch 4 is operated, the controller 5 controls the electric stimulus signal output unit 7 to stop applying a pulse current (electric stimulus) through the electrode 3 to the patient. At the same time, the stop switch 41 transmits a timing signal to the controller 5 to time the controller 5 to recognize the value of the pulse current (electric stimulus) applied through the electrode 3.

When the step-down switch 43 of the remote switch 4 is operated, a step-up control mode changes to a step-down control mode. When the step-up switch 42 of the remote switch 4 is operated, the step-down control mode changes to the step-up control mode. Therefore, the step-up switch 42 and the step-down switch 43 serve as mode selector switches for switching between the step-up control mode and the step-down control mode.

The remote switch 4 and the system assembly 2 communicate with each other through a wired communication link. However, they may communicate with each other through a wireless communication link.

Structural details of the pain measurement system 1 which have not been described above will be described below in connection with operation of the pain measurement system 1.

Operation of the pain measurement system 1 with regard to a process of measuring the magnitude of a pain will be described below.

First, the operator of the pain measurement system 1 with confirms that the patient is not suffering a pain or a disorder such as an inflammation on a region, typically an arm, where the electrode 3 will be mounted. Then, the operator mounts the electrode 3 on an inner side of the forearm of the arm.

The operator operates the start switch (not shown) on the control panel 6 of the system assembly 2.

During a first step, a pulse current whose current value (electric stimulus magnitude) increases gradually (with time) flows from the electric stimulus signal output unit 7 through the electrode 3 into the patient. According to the present embodiment, the current value continuously increases at a predetermined constant rate, e.g., at a rate of 6 $\mu$A/sec.

The current increasing rate is preferably in the range from 3 to 12 $\mu$A/sec. Setting the current increasing rate to a value in the above range allows the pain measurement system 1 to measure pain with accuracy.

The current increasing rate can be adjusted as desired when the operator operates a current increasing rate setting dial (not shown) on the control panel 6.

Depending on various factors such as conditions of the patient, the operator can operate the current increasing rate setting dial to set the current increasing rate to an appropriate value.

Then, when the patient receives the pulse current as a stimulus for the first time, the patient operates the stop switch 41 of the remote switch 4.

The electric stimulus signal output unit 7 now stops outputting the pulse current, so that the pulse current stops being applied to the patient. The controller 5 recognizes the stoppage of the pulse current and detects the current value at the time when the stop switch 41 is operated. Specifically, when the stop switch 41 is operated, the remote switch 4 sends a first timing signal to the controller 5. During a second step, when the controller 5 receives this first signal, the controller 5 detects the current value of the pulse current flowing through the electrode 3 into the patient, stores the detected current value as a minimum sensed current value (first stimulus value) in the memory 9, and displays the detected current value on the display unit 8.

It is assumed that the minimum sensed current value is represented by "X".

Then, the operator operates the start switch (not shown) on the control panel 6. In a third step, the controller 5 performs the step-up control mode in which the electric stimulus signal output unit 7 applies a pulse current whose current value increases stepwise by nX (n represents a positive rational number) from a predetermined initial value through the electrode 3 to the patient. The initial value is preferably 2nX.

Specifically, if the initial value is 2nX, then a pulse current whose current value increases stepwise by 2n, 3n, 4n, 5n, . . . times the minimum sensed current value and persists as a certain current value (current intensity) flows through the electrode 3 into the patient. For example, if n is set to 1, then a pulse current which increases stepwise by 2, 3, 4, 5, . . . times the minimum sensed current value flows through the electrode 3 into the patient.

According to the present embodiment, the current value increases at a certain constant rate.

The period of the pulse current is small compared with the time during which the current value persists in each step, and hence the waveform of the pulse current is not illustrated.

The value of n (n value) is preferably in the range from 0.1 to 2.0. Setting the n value to a value in that range allows the pain measurement system 1 to measure pain accurately and quickly.

The n value can be adjusted as desired when the operator operates an n value setting dial (not shown) on the control panel 6. Depending on various conditions such as conditions of the patient and the degree of the pain to be measured, the operator can operate the n value setting dial to set the n value to an appropriate value.

For example, if the magnitude of a subtle pain, e.g., the magnitude of a pain caused by the penetration of a extremely thin needle, is to be measured, then the n value is preferably set to a value equal to or smaller than 1. Specifically, the n value is set to 0.5, for example, and multiples for stepping up the n value are set to 1.0, 1.5, 2,0, 2.5, etc. to reduce step-up intervals.

The time during which the current value (electric stimulus magnitude) stays in each step should preferably be in the range from 1 to 30 seconds. If the time during which the current value stays in each step is set to a value in that range, then the pain measurement system 1 can measure pain quickly and reliably.

The time during which the current value stays in each step can be adjusted as desired when the operator operates a time setting dial (not shown) on the control panel 6. Depending on various conditions such as conditions of the patient and the period of the pain to be measured, the operator can operate the time setting dial to set the time during which the current value stays in each step to an appropriate value.

The measurement process can be interrupted temporarily. Specifically, when the operator operates the pause switch (not shown) on the control panel 6, the electric stimulus signal output unit 7 temporarily interrupts the outputting of the pulse current, so that the application of the pulse current to the patient is interrupted temporarily.

The patient receives a temporary pain in a region different from the arm on which the electrode 3 is mounted. The patient compares the magnitude of the received temporary pain and the magnitude of a current sensation (electric stimulus sensation) having a certain intensity which are being simultaneously perceived with each other. If the patient judges that the compared magnitudes are the same as each other, then the patient operates the stop switch 41 of the remote switch 4.

In a fourth step, the electric stimulus signal output unit 7 now stops outputting the pulse current, so that the pulse current stops being applied to the patient. The controller 5 recognizes the stoppage of the pulse current and detects the current value at the time when the stop switch 41 is operated. Specifically, when the stop switch 41 is operated, the remote switch 4 sends a second timing signal to the controller 5. When the controller 5 receives this second signal, the controller 5 detects the current value of the pulse current flowing through the electrode 3 into the patient, stores the detected current value as a pain-commensurate current value (second stimulus value) in the memory 9, and displays the detected current value on the display unit 8. The controller 5 stores a value, which is produced by dividing the pain-commensurate current value by the minimum sensed current value, as a pain ratio value in the memory 9, and displays the pain ratio on the display unit 8.

The patient compares the magnitude of the temporary pain and the magnitude of the current sensation with each other. If the patient judges that the magnitude of the current sensation is greater than the magnitude of the temporary pain, then the patient operates the step-down switch 43 of the remote switch 4.

The controller 5 then starts the step-down control mode, i.e., switches from the step-up control mode to the step-down control mode, in which the electric stimulus signal output unit 7 applies a pulse current whose current value decreases stepwise by nX from the value at the end of the step-up control mode through the electrode 3 to the patient (third step).

When the step-up control mode switches to the step-down control mode, the n value is changed to a value smaller than that which was used before the step-up control mode switched to the step-down control mode. The decrease per step in the current value is thus made smaller, allowing the patient to compare the actual pain with the current stimulus accurately and reliably.

If the n value is set to 1 in the step-up control mode and the current value at the end of the step-up control mode is 4x, then in the step-down control mode, the n value is set to 0.5, for example. A pulse current whose current value decreases stepwise by 3.5, 3, 2.5, . . . times the minimum sensed current value and persists as a certain current value (current intensity) flows through the electrode 3 into the patient.

According to the present embodiment, the current value can first decrease at a certain constant rate.

Then, in the same manner as described above, the patient receives a temporary pain in a region different from the arm on which the electrode 3 is mounted. The patient compares the magnitude of the received temporary pain and the magnitude of a current sensation (electric stimulus sensation) having a certain intensity which are being simultaneously perceived with each other. If the patient judges that the compared magnitudes are the same as each other, then the patient operates the stop switch 41 of the remote switch 4. Subsequent operation is the same as described above.

When the patient compares the magnitude of the received temporary pain and the magnitude of the current sensation with each other, if the patient judges that the magnitude of the current sensation is smaller than the magnitude of the temporary pain, then the patient operates the step-up switch 42 of the remote switch 4.

The controller 5 then starts the step-up control mode again, i.e., switches from the step-down control mode to the step-up control mode, in which the electric stimulus signal output unit 7 applies a pulse current whose current value increases stepwise by nX from the value at the end of the step-down control mode through the electrode 3 to the patient.

When the step-down control mode switches to the step-up control mode, the n value is changed to a value smaller than that which was used before the step-down control mode switched to the step-up control mode. The increase per step in the current value is thus made smaller, allowing the pain measurement system 1 to measure pain accurately and reliably.

Subsequently, the step-up control mode and the step-down control mode will alternately be repeated until the patient judges that the magnitude of the received temporary pain and the magnitude of the current sensation (electric stimulus sensation) which are being simultaneously perceived are the same as each other and operates the stop switch 41 of the remote switch 4.

If the n value becomes less than 0.1 when one of the step-up control mode and the step-down control mode switches to the other, the time of the mode switching is regarded as the time when the magnitude of the temporary pain and the magnitude of the current sensation are substantially the same as each other.

With the pain measurement system 1, the maximum value of the pulse current that flows into the patient is limited to a predetermined value for increased safety. The maximum value is preferably 10x.

For higher safety, the pain measurement system 1 stops applying the pulse current to the patient even if the pulse current is lower than the maximum value 10x when the effective current value of the pulse current flowing into the patient exceeds 160 µA.

The above process of stepping up the pulse current after it is stepped down may be replaced with the following process: When the current value increases stepwise until the patient judges that the magnitude of the current sensation (electric stimulus sensation) approaches the magnitude of the actual temporary pain and operates a certain control switch of the remote switch 4, the step-up (stepwise increasing) control mode for increasing the current value stepwise changes to a continuously increasing control mode for continuously increasing the current value to search for the magnitude of the current sensation (electric stimulus sensation) which corresponds to the pain. This process makes it possible to measure pain in a relatively short period of time.

The reason why the values of the step-up current or the step-down current flowing into the patient are multiples, e.g., 2n, 3n, . . . , of the minimum sensed current value is that the sensation for sensing a current (electric stimulus) greatly differs from individual to individual and such an individual difference should be as small as possible.

A person who is insensitive to a current is also insensitive to a pulse current to be compared with a temporary pain. Therefore, if an increase per step in a preset current value is relatively small, then it takes a long period of time for the current value to reach a magnitude that the person feels as being equivalent to the temporary pain. On the other hand, a person who is sensitive to a current is also sensitive to a pulse current to be compared with a temporary pain. Therefore, if an increase per step in a preset current value is relatively large, then the current value may exceed a magnitude that the person feels as being equivalent to the temporary pain. It also holds true for a decrease per step in the current value.

Figure 4:
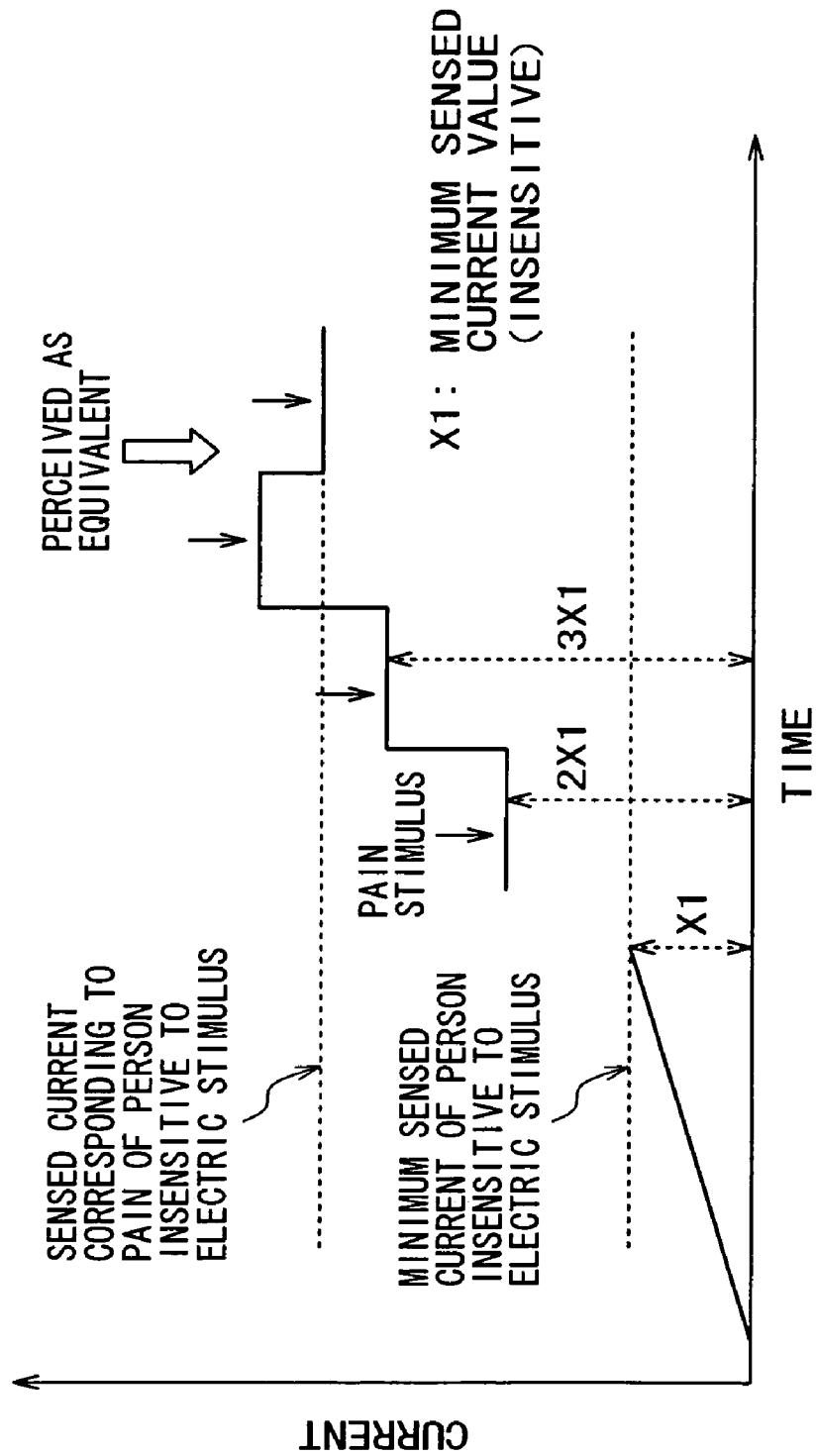
FIG. 4 is a diagram illustrative of the manner in which the pain measurement system shown in FIG. 1 operates to measure a magnitude of pain in a patient who is insensitive to a current (electric stimulus) if the value of n is set to 1.
Figure 5:
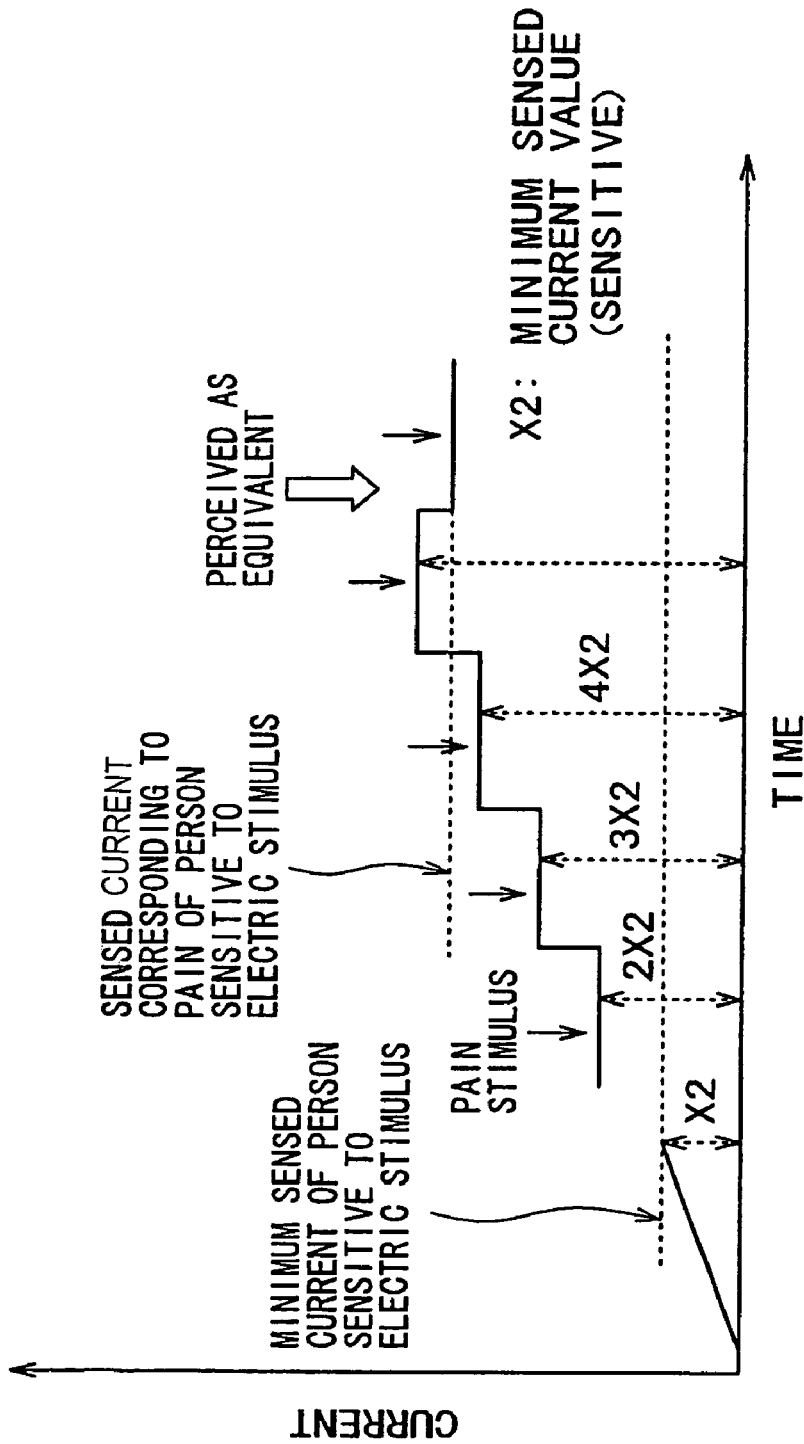
FIG. 5 is a diagram illustrative of the manner in which the pain measurement system shown in FIG. 1 operates to measure a magnitude of pain in a patient who is sensitive to a current (electric stimulus) if the value of n is set to 1.

By increasing or decreasing the current value stepwise by nX, the pain measurement system 1 offers the following advantages:

FIG. 4 is illustrative of the manner in which the pain measurement system 1 shown in FIG. 1 operates to measure a magnitude of pain in a patient who is insensitive to a current (electric stimulus) if the n value is set to 1, and FIG. 5 is illustrative of the manner in which the pain measurement system 1 shown in FIG. 1 operates to measure a magnitude of pain in a patient who is sensitive to a current (electric stimulus) if the n value is set to 1.

As shown in FIG. 4, the patient who is insensitive to a current (electric stimulus) experiences a high current value corresponding to a pain and also a high minimum sensed current value (X1). Therefore, the current value increases stepwise by the high value X1 and reaches a current value corresponding to the pain in a relatively short period of time.

On the contrary, as shown in FIG. 5, the patient who is sensitive to a current (electric stimulus) experiences a low current value X2 corresponding to a pain. The current value increases stepwise by a low minimum sensed current value X2. Consequently, the current value reaches a current value corresponding to the pain in a relatively short period of time. As the current value steps up by smaller intervals, the current is prevented from exceeding the current value corresponding to the pain.

In this manner, measuring time variations among individuals who are differently sensitive to currents can be reduced.

The following experiment was conducted:

The pain measurement system 1 was used to measure the magnitude of a temporary heat-induced pain on a total of 18 examinees who were all adults (7 males and 11 females, the average age: 27.3).

A temporary heat-induced pain to be experimentally experienced by the examinees was produced by burning small amounts of "moxa" (doses of 0.4 g, 0.6 g, and 1.0 g) on a base of aluminum foil held in contact with the skin. The "moxa" that was used was "Cut moxa" (YAMASHO Co., Ltd.). After the "moxa" was weighed, each dose was rounded into a certain size. The base of aluminum foil was of a circular shape having a diameter of 6 mm which was coated with an adhesive on its skin contacting surface. All doses of the "moxa" were burned up in a few seconds on the base of aluminum foil.

Figure 6:
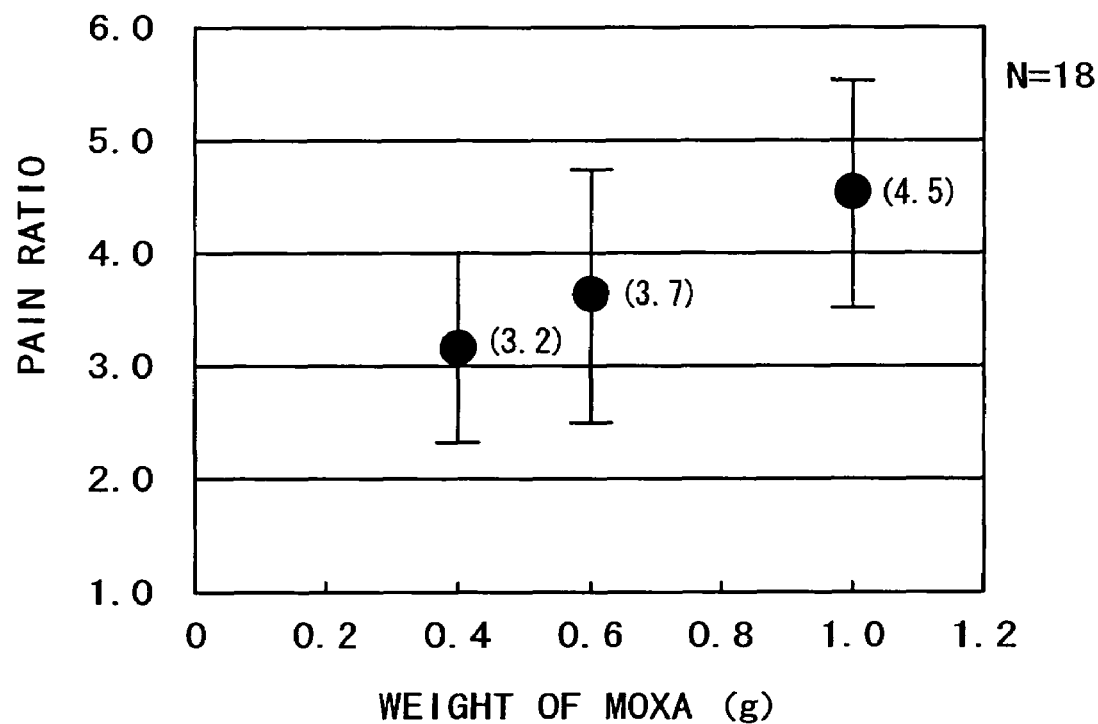
FIG. 6 is a graph showing the results of an experiment conducted to measure temporary pain with the pain measurement system shown in FIG. 1.

The results of the experiment are shown in FIG. 6. In this figure, the solid dots represent average values and the vertical bars represent standard deviations.

The average values of pain ratios at the time the "moxa" in the doses of 0.4 g, 0.6 g, and 1.0 g was burned were 3.2, 3.7, and 4.5, respectively. Therefore, it is seen that the magnitude of pain experienced when the "moxa" is burned increases depending on the weight of the "moxa". Though the experimentally produced temporary pain and the sensation of an electric stimulus are qualitatively different from each other, the measured results were reproducible, and it was confirmed that the pain measurement system 1 is capable of measuring the magnitude of temporary pain accurately and reliably.

As described above, the pain measurement system 1 increases the magnitude of an electric stimulus (particularly, a painless stimulus) applied in the form of a pulse current to a patient (examinee), stepwise by nX (X represents a minimum sensed stimulus value, n represents a positive rational number), thereby holding the electric stimulus for a given period of time. Therefore, the pain measurement system 1 is capable of measuring, accurately and reliably, the magnitude of not only sustained pain, but also temporary pain which continues for only a few seconds.

Since the pain measurement system 1 increases the stimulus stepwise by nX, it can measure the magnitude of pain accurately and reliably while reducing measuring time variations among individuals who have different sensitivities to stimuli.

Because the pain measurement system 1 can selectively perform the step-up control mode for increasing the magnitude of a stimulus stepwise and the step-down control mode for decreasing the magnitude of a stimulus stepwise, the magnitude of an electric stimulus and the magnitude of a pain can be compared as many times as desired for increased measuring accuracy.

Inasmuch as the pain measurement system 1 applies a painless electric stimulus to the patient to measure the magnitude of a pain felt by the patient, the burden imposed on the patient for pain measurement can be reduced.

As the pain measurement system 1 can measure a temporary pain, it can easily and reliably measure the magnitude of a periodic pain, e.g., a headache (cluster headache, trigeminal neuralgia), birth pains, etc., and the magnitude of a human-induced pain, e.g., a penetration pain caused by a penetrating needle for use in various applications such as hypodermic injection, venous blood specimen collection, etc., or an insertion pain caused by an urethral catheter.

Patterns for increasing or decreasing a stimulus value such as a current value stepwise are not limited to those described above, but may be other patterns.

For example, in the step-up control mode for increasing the current value stepwise, the n value may be decreased gradually. In this manner, the increase per step in the current value may be reduced gradually for measuring the magnitude of pain more accurately and reliably.

In the step-down control mode for decreasing the current value stepwise, the n value may be decreased gradually. In this manner, the decrease per step in the current value may be reduced gradually for measuring the magnitude of pain more accurately and reliably.

In the step-up control mode for increasing the current value stepwise, the time during which the current value stays in each step may be decreased gradually. In this manner, the measuring time may be shortened.

In the step-up control mode for increasing the current value stepwise, the time during which the current value stays in each step may be shorter than in the preceding step-down control mode. In this manner, the measuring time may be shortened.

In the step-up control mode for increasing the current value stepwise, the time during which the current value stays in each step may be increased gradually.

In this manner, the magnitude of pain can be measured more accurately and reliably.

In the step-up control mode for increasing the current value stepwise, the time during which the current value stays in each step may be longer than in the preceding step-down control mode. In this manner, the magnitude of pain can be measured more accurately and reliably.

In the step-down control mode for decreasing the current value stepwise, the time during which the current value stays in each step may be decreased gradually. In this manner, the measuring time may be shortened.

In the step-down control mode for decreasing the current value stepwise, the time during which the current value stays in each step may be shorter than in the preceding step-up control mode. In this manner, the measuring time may be shortened.

In the step-down control mode for decreasing the current value stepwise, the time during which the current value stays in each step may be increased gradually. In this manner, the magnitude of pain can be measured more accurately and reliably.

In the step-down control mode for decreasing the current value stepwise, the time during which the current value stays in each step may be longer than in the preceding step-up control mode. In this manner, the magnitude of pain can be measured more accurately and reliably.

According to the present invention, the controller 5 may be arranged to have means for or a step of controlling the electric stimulus signal output unit 7 to apply a pulse current (stimulus) having a substantially constant current value through the electrode 3, means for or a step of controlling the electric stimulus signal output unit 7 to stop applying the pulse current through the electrode 3, and means for or a step of controlling the electric stimulus signal output unit 7 to start applying a pulse current having a current value which is greater by a predetermined amount than before the pulse current stops being applied.

The controller 5 may be arranged to control the electric stimulus signal output unit 7 to stop applying the pulse current through the electrode 3 when a certain control switch of the remote switch 4 is operated, and to start applying the pulse current through the electrode 3 when a certain control switch of the remote switch 4 is subsequently operated.

With this arrangement, even if the patient experiences a certain pain for the measurement of pain, the burden on the patient can be reduced because the application of the pulse current through the electrode 3 can be stopped in the measuring process.

In the present embodiment, the applied stimulus is an electric stimulus, and the stimulus applying means is an electrode. However, the present invention is not limited to those specific details.

According to the present invention, the applied stimulus may be a vibratory stimulus, and the stimulus applying means may be a vibrating device for applying vibratory stimulus.

With such a modification, the pain measurement system has a vibrating device for applying vibratory stimulus, an electric power supply (energy supply) for supplying electric power (electric energy) to the vibrating device, a control unit for controlling the electric power supply, and a remote switch (console) for transmitting first and second signals to the control unit to cause the control unit to recognize the value of the vibratory stimulus applied by the vibrating device. The vibratory stimulus can reduce the burden on the patient as it does not cause a pain for the measurement process.

Other structural details, operation, and advantages of the pain measurement system thus modified are the same as those described above with respect to the present embodiment, and will not be described in detail below.

A pain measurement system according to a second embodiment of the present invention will be described below.

Figure 7:
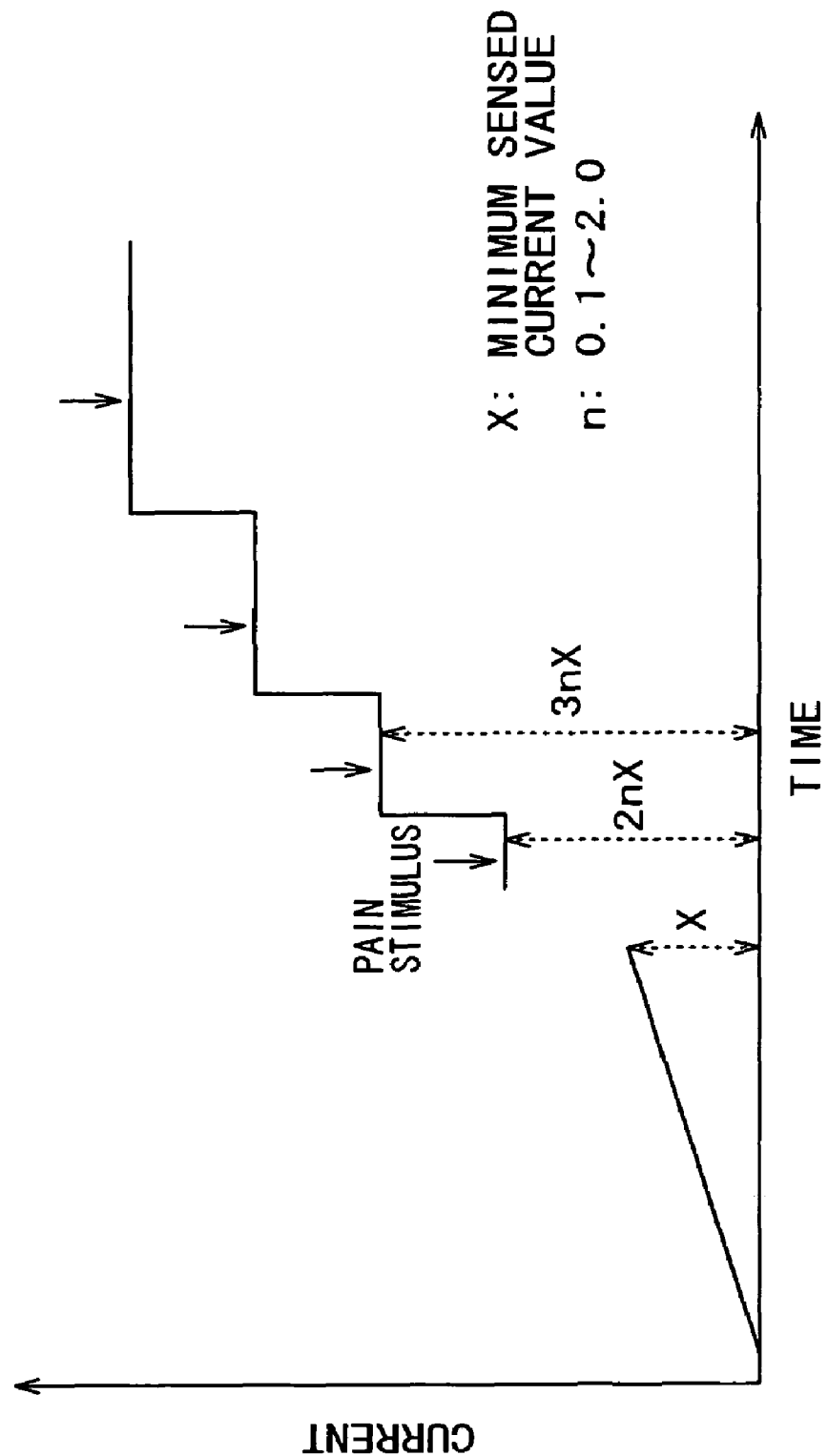
FIG. 7 is a diagram illustrative of the manner in which a pain measurement system according to a second embodiment of the present invention operates.

FIG. 7 is a diagram illustrative of the manner in which the pain measurement system according to the second embodiment of the present invention operates.

The pain measurement system, also denoted by 1, according to the second embodiment will be described below basically with respect to differences with the pain measurement system according to the first embodiment. Those details of the pain measurement system 1 according to the second embodiment which are the same as the pain measurement system according to the first embodiment will not be described in detail below.

The pain measurement system 1 according to the second embodiment operates in the third step as follows: In the step-up control mode, the current value of a pulse current (the magnitude of a stimulus) increases stepwise by nX, and the time during which it stays in each step changes, and in the step-down control mode, the current value of the pulse current decreases stepwise by nX, and the time during which it stays in each step changes.

The pain measurement system 1 according to the second embodiment is also arranged such that in the third step, the time during which the current value of a pulse current (the magnitude of a stimulus) stays in each step increases gradually. Specifically, the pain measurement system 1 may be arranged as follows:

If n=1, for example, then the time (initial value) during which the current value of the pulse current stays in the first step is 10 seconds, and the time during which it stays increases by 5 seconds in each step (10 seconds, 15 seconds, 20 seconds, 25 seconds, . . . ) until it reaches a maximum of 30 seconds. If n=0.1, for example, then the time (initial value) during which the current value of the pulse current stays in the first step is 1 second, and the time during which it stays increases by 0.5 second in each step (1 second, 1.5 seconds, 2 seconds, 2.5 seconds, . . . ) until it reaches a maximum of 30 seconds. These numerical values are given by way of example only, and hence the present invention is not limited to those numerical values.

The pain measurement system 1 according to the second embodiment offers the following advantages: The time during which the current value of the pulse current flowing into the patient stays in each step increases gradually to give a margin to the time required to compare the magnitude of a temporary pain and the magnitude of a current sensation with each other as the magnitude of the current sensation approaches the magnitude of the temporary pain. Thus, when the magnitude of the temporary pain and the magnitude of the current sensation become equal to each other, the patient can recognize, without fail, the time to operate the stop switch 41, and can operate the stop switch 41 appropriately for measuring the pain accurately and reliably.

The pain measurement system 1 according to the second embodiment also offers the same advantages as those of the pain measurement system 1 according to the first embodiment.

A pain measurement system according to a third embodiment of the present invention will be described below.

Figure 8:
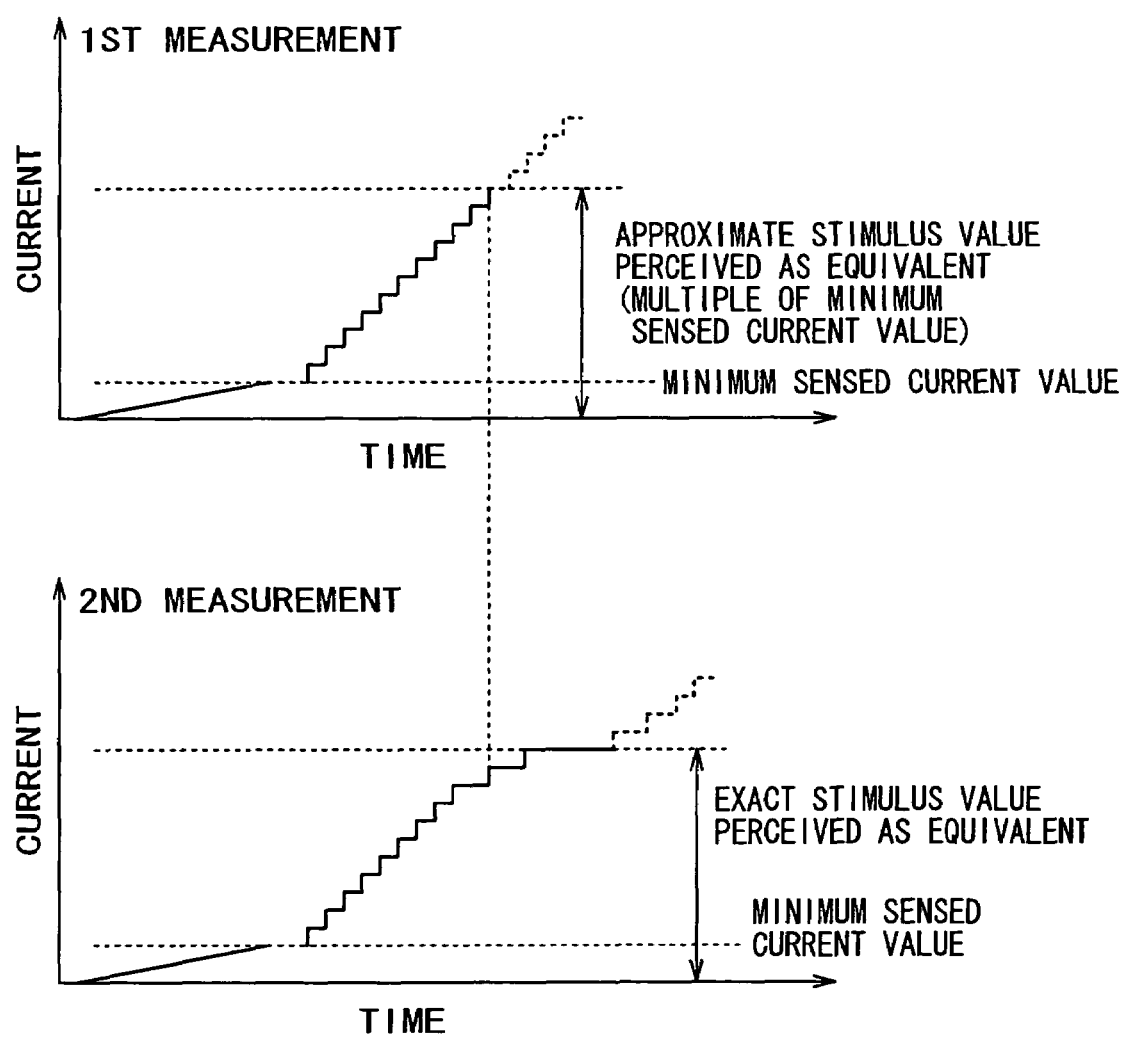
FIG. 8 is a diagram illustrative of the manner in which a pain measurement system according to a third embodiment of the present invention operates.

FIG. 8 is a diagram illustrative of the manner in which the pain measurement system according to the third embodiment of the present invention operates.

The pain measurement system, also denoted by 1, according to the third embodiment will be described below basically with respect to differences with the pain measurement system according to the first embodiment. Those details of the pain measurement system 1 according to the third embodiment which are the same as the pain measurement system according to the first embodiment will not be described in detail below.

The pain measurement system 1 according to the third embodiment performs a measuring process at least twice.

For example, if the pain measurement system 1 performs a measuring process twice, then, in the first measuring process, the current value of a pulse current increases at a substantially constant rate to determine a pain-commensurate current value (first stimulus value) roughly, i.e., to obtain a general pain-commensurate current value.

Specifically, when the stop switch 41 is operated, the remote switch 4 sends a first signal to the controller 5. When the controller 5 receives the first signal, the controller 5 detects the current value of the pulse current flowing through the electrode 3 into the patient, stores the detected current value as a pain-commensurate current value (first stimulus value) in the memory 9, and displays the detected current value on the display unit 8.

Then, in the second measuring process, before the current value of the pulse current (the magnitude of the stimulus) reaches the first stimulus value, the rate at which the current value of the pulse current increases is made smaller than the rate at which the current value of the pulse current increases in the first measuring process. For example, in the second measuring process, before the current value of the pulse current reaches the first stimulus value, the time during which the current values stays in each step is increased, and after the current value of the pulse current exceeds the first stimulus value, the time during which the current values stays in each step is returned to the original period. Then, in the second measuring process, a pain-commensurate current value (second stimulus value) is determined accurately.

Specifically, when the stop switch 41 is operated, the remote switch 4 sends a second signal to the controller 5. When the controller 5 receives the second signal, the controller 5 detects the current value of the pulse current flowing through the electrode 3 into the patient, stores the detected current value as a pain-commensurate current value (second stimulus value) in the memory 9, and displays the detected current value on the display unit 8. The controller 5 also stores a value, which is produced by dividing the pain-commensurate current value by the minimum sensed current value, as a pain ratio value in the memory 9, and displays the value on the display unit 8.

The pain measurement system 1 according to the third embodiment offers the following advantages: In the first measuring process, since the pain-commensurate current value is roughly determined, the rate at which the current value of the pulse current increases can be increased to thereby reduce the measuring time. In the second measuring process, the time during which the current value of the pulse current stays in each step is increased before the current value reaches the first stimulus value. Therefore, a margin is given to the time required to compare the magnitude of a temporary pain and the magnitude of a current sensation with each other for measuring the pain accurately and reliably.

The pain measurement system 1 according to the third embodiment also offers the same advantages as those of the pain measurement system 1 according to the first embodiment.

A pain measurement system according to a fourth embodiment of the present invention will be described below.

FIG. 9 is a diagram illustrative of the manner in which the pain measurement system according to the fourth embodiment of the present invention operates.

The pain measurement system, also denoted by 1, according to the fourth embodiment will be described below basically with respect to differences with the pain measurement system according to the first embodiment. Those details of the pain measurement system 1 according to the fourth embodiment which are the same as the pain measurement system according to the first embodiment will not be described in detail below.

The pain measurement system 1 according to the fourth embodiment performs a measuring process at least twice.

In the first measuring process, the current value of a pulse current (the magnitude of a stimulus) increases irregularly with time to determine a pain-commensurate current value (first stimulus value).

Specifically, when the stop switch 41 is operated, the remote switch 4 sends a first signal to the controller 5. When the controller 5 receives the first signal, the controller 5 detects the current value of the pulse current flowing through the electrode 3 into the patient, stores the detected current value as a pain-commensurate current value (first stimulus value) in the memory 9, and displays the detected current value on the display unit 8. The controller 5 also stores a value, which is produced by dividing the pain-commensurate current value by the minimum sensed current value, as a pain ratio value in the memory 9, and displays the value on the display unit 8.

In the first measuring process, the current value of the pulse current increases stepwise, and the increase per step in the current value and/or the time during which the current value stays in each step preferably increase and decrease irregularity.

In the second measuring process, the current value increases with time to cause the current value of the pulse current to reach the first stimulus value with time which is different from the time required for the current value of the pulse current to reach the first stimulus value in the first measuring process. In the second measuring process, a pain-commensurate current value (second stimulus value) is determined.

Specifically, when the stop switch 41 is operated, the remote switch 4 sends a second signal to the controller 5. When the controller 5 receives the second signal, the controller 5 detects the current value of the pulse current flowing through the electrode 3 into the patient, stores the detected current value as a pain-commensurate current value (second stimulus value) in the memory 9, and displays the detected current value on the display unit 8. The controller 5 also stores a value, which is produced by dividing the pain-commensurate current value by the minimum sensed current value, as a pain ratio value in the memory 9, and displays the value on the display unit 8.

In the second measuring process, the current value of the pulse current increases stepwise, and the increase per step in the current value and the time during which the current value stays in each step should preferably increase and decrease irregularity.

A patient who is taking a painkiller such as an opioid-based analgetic agent (narcotic analgetic agent) or a patient who tends to overemphasize his or her pain can be expected to report a pain with a falsified magnitude.

With the pain measurement system 1 according to the fourth embodiment, in the second measuring process, the current value of the pulse current reaches the first stimulus value in a time which is different from the time required for the current value of the pulse current to reach the first stimulus value in the first measuring process. Therefore, if the patient operates the stop switch 41 of the remote switch 4 at a random (falsified) time, then no reproducibility is obtained in the second measuring process.

If there is a large difference between pain-commensurate current values, i.e., pain ratio values, in the first and second measuring processes, then a third measuring process is carried out. If there is a large difference between pain-commensurate current values, i.e., pain ratio values, in the second and third measuring processes, then a fourth measuring process is carried out. A measuring process is subsequently repeated until pain-commensurate current values, i.e., pain ratio values, in two successive measuring processes become close to each other. In this manner, the pain can accurately be measured.

The pain measurement systems according to the preferred embodiments have been described above. However, the present invention is not limited to those specific details. The components of the pain measurement systems may be replaced with other components having identical functions, and other components and processes may be added to the above pain measurement systems.

Components or features of at least two of the pain measurement systems according to the preferred embodiments may be combined with each other.

Although certain preferred embodiments of the present invention have been shown and described in detail, it should be understood that various changes and modifications may be made therein without departing from the scope of the appended claims.

What is claimed is:

1. A pain measurement system for measuring a magnitude of pain experienced by an examinee, comprising:
    means for applying a stimulus;
    an output unit that outputs a stimulus to said stimulus applying means;
    a control unit that controls an output of said output unit; and
    a console that sends a signal to said control unit to cause said control unit to recognize the value of the stimulus applied by said stimulus applying means;

said control unit comprising:
first means for controlling said output unit to cause said stimulus applying means to apply a stimulus having a magnitude which increases with time;
second means for recognizing the value of the stimulus applied by said stimulus applying means as a first stimulus value when a first signal is received from said console;
third means for controlling said output unit to cause said stimulus applying means to apply a stimulus having a magnitude which increases from a predetermined initial value stepwise by nX where X represents said first stimulus value and n represents a positive rational number having a value in the range from 0.1 to 2.0; and
fourth means for recognizing the value of the stimulus applied by said stimulus applying means as a second stimulus value when a second signal is received from said console.

2. The pain measurement system of claim 1, wherein said third means includes a step-up control mode for controlling the output unit to cause the stimulus applying means to apply a stimulus having a magnitude which increases from a predetermined initial value stepwise by nX, and a step-down control mode for controlling the output unit to cause the stimulus applying means to apply a stimulus having a magnitude which decreases stepwise by nX.

3. The pain measurement system of claim 2, wherein said third means performs the step-up control mode prior to performing said step-down control mode.

4. The pain measurement system of claim 2, wherein said third means reduces the value of n when switching from one of the step-up control mode and the step-down control mode to the other.

5. The pain measurement system of claim 2, wherein said console includes a stop switch for causing the stimulus applying means to stop applying the stimulus, and a mode selector switch for switching from one of the step-up control mode and the step-down control mode to the other.

6. A method of measuring a magnitude of pain experienced by an examinee with a pain measurement system having means for applying a stimulus, an output unit for outputting a stimulus to said stimulus applying means, a control unit for controlling an output of said output unit, and a console for sending a signal to said control unit to cause said control unit to recognize the value of the stimulus applied by said stimulus applying means, said method comprising the steps of:
controlling said output unit to cause said stimulus applying means to apply a stimulus having a magnitude which increases with time;
recognizing the value of the stimulus applied by said stimulus applying means as a first stimulus value when a first signal is received from said console;
controlling said stimulus output unit to cause said stimulus applying means to apply a stimulus having a magnitude which increases from a predetermined initial value stepwise by nX where X represents said first stimulus value and n represents a positive rational number having a value in the range from 0.1 to 2.0; and
recognizing the value of the stimulus applied by said stimulus applying means as a second stimulus value when a second signal is received from said console.

7. A method of measuring a magnitude of pain experienced by an examinee, said method comprising the steps of:
applying a stimulus having a magnitude which increases with time;
recognizing the value of the stimulus as a first stimulus value when the examinee senses a stimulus for the first time;
applying a stimulus having a magnitude which increases from a predetermined initial value stepwise by nX where X represents said first stimulus value and n represents a positive rational number having a value in the range from 0.1 to 2.0;
comparing a magnitude of the stimulus to the magnitude of pain experienced by the examinee; and
recognizing the value of the stimulus as a second stimulus value when the examinee judges that the compared magnitudes are the same as each other.

8. The method of claim 7, further including the step of switching from a first mode in which the magnitude of said stimulus increases over time to a second mode in which the magnitude of said stimulus decreases over time during said second applying step.

9. The method of claim 8, further including the step of reducing the value of n when switching from one of said modes to the other of said modes.

10. The method of claim 7, further including the step of varying the duration of said steps during said second applying step.

11. The method of claim 10, wherein the duration of said steps increase over time.

12. The method of claim 10, wherein the duration of said steps vary in an irregular manner.

13. The method of claim 7, further including the steps of:
after recognizing said second stimulus value, applying a stimulus having a magnitude which increases stepwise by nX; and
increasing the duration of said steps as the magnitude of said stimulus approaches said second stimulus value.

14. The method of claim 7, further including the steps of:
varying at least one of the value of n and the duration of the steps during said second applying step, to cause said stimulus to increase in an irregular manner;
after recognizing said second stimulus value, performing a third applying step in which a stimulus is applied with a magnitude that increases over time in an irregular manner different from said second applying step;
comparing the magnitude of the stimulus during said third applying step to the magnitude of pain experienced by the examinee; and
recognizing the value of the stimulus as a third stimulus value when the examinee judges that the compared magnitudes are the same as each other.

15. The method of claim 14, further including the steps of:
comparing said third stimulus value to said second stimulus value to determine whether the difference between them is within a predetermined range; and
if said difference is not within said range, repeating said applying steps in which a stimulus is applied that increases over time in an irregular manner, until at least two stimulus values are recognized whose difference is within said range.

16. The method of claim 15, wherein said applying steps are repeated until two successive stimulus values are recognized whose difference is within said range.

17. The method of claim 14, wherein the magnitude of said stimulus reaches said second stimulus value in a different amount of time during said third applying step than it does during said second applying step.

* * * * *